United States Patent [19]

Lester

[11] 4,333,450
[45] Jun. 8, 1982

[54] NEBULIZER-MANIFOLD

[76] Inventor: Victor E. Lester, P.O. Box 608, Sonora, Calif. 95370

[21] Appl. No.: 139,259

[22] Filed: Apr. 11, 1980

Related U.S. Application Data

[63] Continuation of Ser. No. 750,510, Dec. 14, 1976, abandoned, which is a continuation-in-part of Ser. No. 635,902, Nov. 28, 1975, abandoned, which is a continuation-in-part of Ser. No. 523,123, Nov. 12, 1974, abandoned.

[51] Int. Cl.³ ............................................. A61M 11/00
[52] U.S. Cl. .......................... 128/200.14; 128/200.18; 128/205.24
[58] Field of Search ....................... 128/200.14, 200.18, 128/200.21, 205.24, 205.25, 205.13, 204.25

[56] References Cited

U.S. PATENT DOCUMENTS

| | | | |
|---|---|---|---|
| 2,785,768 | 3/1957 | Gauchard | 128/200.14 |
| 2,841,142 | 7/1958 | Hay | 128/205.24 X |
| 2,985,169 | 5/1961 | Elling | 128/205.24 |
| 3,010,910 | 11/1961 | Gauchard | 128/200.21 |
| 3,097,645 | 7/1963 | Lester | 128/200.21 |
| 3,234,932 | 2/1966 | Bird et al. | 128/204.25 |
| 3,265,061 | 8/1966 | Gage, Jr. | 128/204.28 |
| 3,502,297 | 3/1970 | Wardrup | 251/61.1 |
| 3,580,249 | 5/1971 | Takaoka | 128/200.14 |
| 3,664,337 | 5/1972 | Lindsey et al. | 128/200.18 |
| 3,762,409 | 10/1973 | Lester | 128/200.14 |
| 3,796,216 | 3/1974 | Schwarz | 128/205.13 |
| 3,814,091 | 6/1974 | Henkin | 128/202.22 |
| 3,826,255 | 7/1974 | Havstad et al. | 128/200.18 |
| 3,874,379 | 4/1975 | Enfield et al. | 128/200.18 |

FOREIGN PATENT DOCUMENTS 548068 9/1956 Italy ................................. 128/200.18

Primary Examiner—Henry J. Recla
Attorney, Agent, or Firm—Manfred M. Warren; Robert B. Chickering; Glen R. Grunewald

[57] ABSTRACT

A disposable nebulizer-manifold device which produces aerosol includes a manifold body and a nebulizer unit having a nozzle assembly. The manifold body includes a main supply inlet, exhalation outlet, and a patient connector port. Within the manifold body is a diaphragm assembly which controls the exhalation port.

7 Claims, 11 Drawing Figures

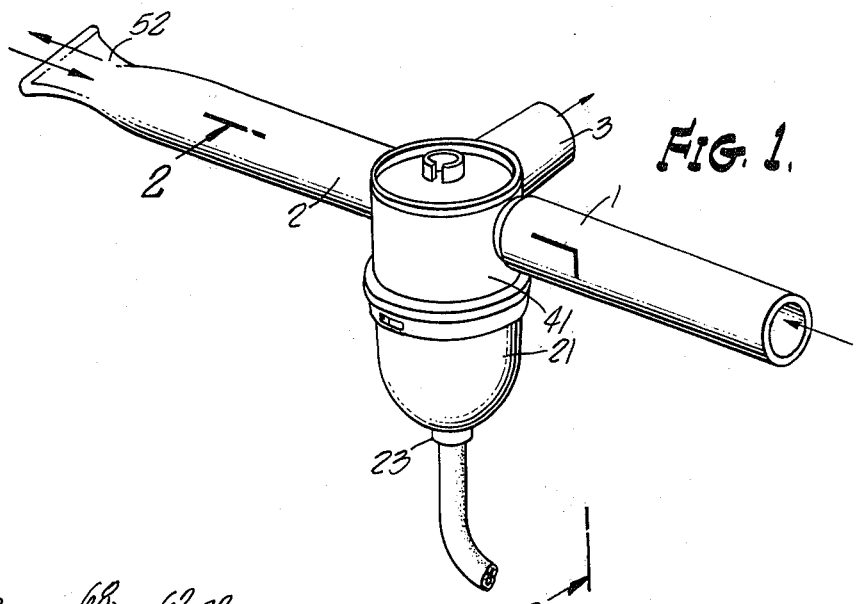
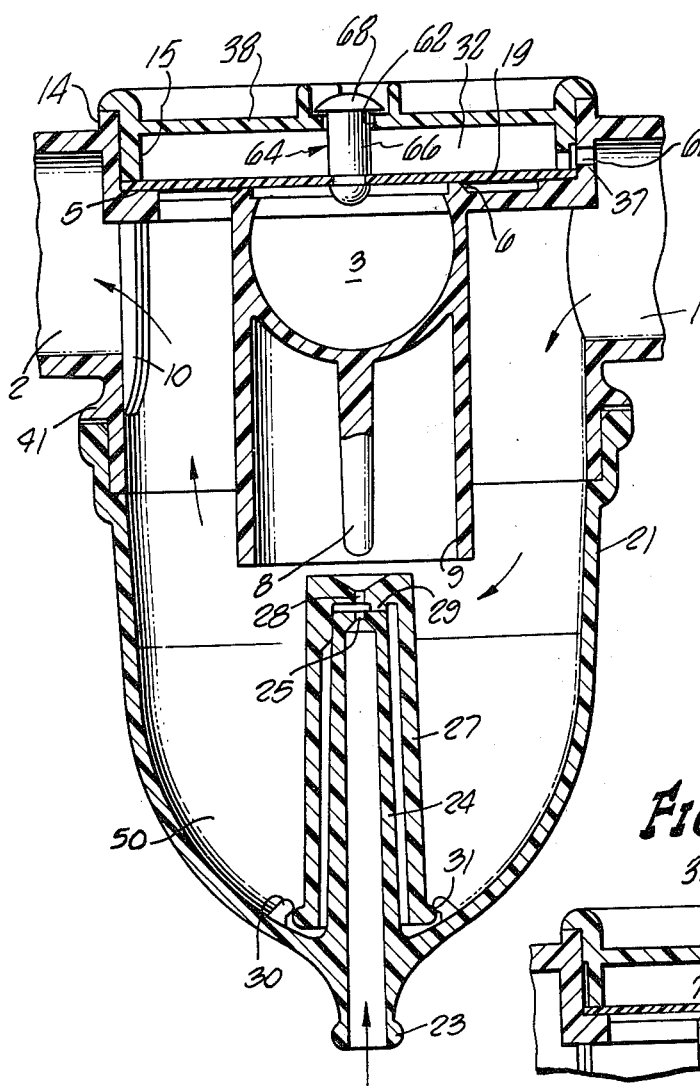
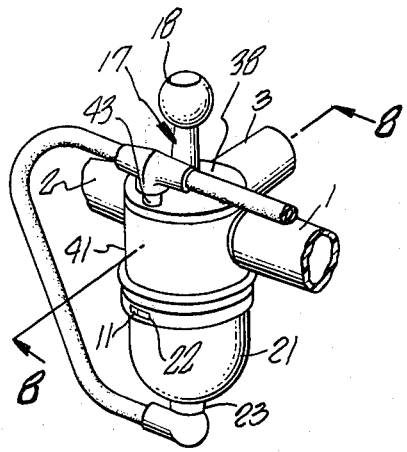
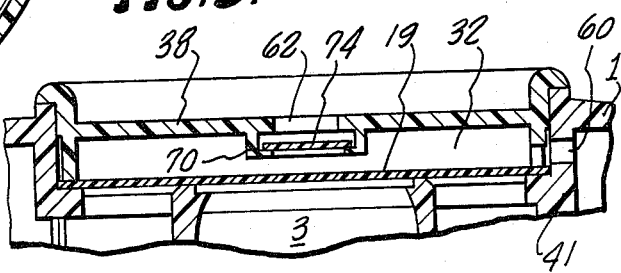

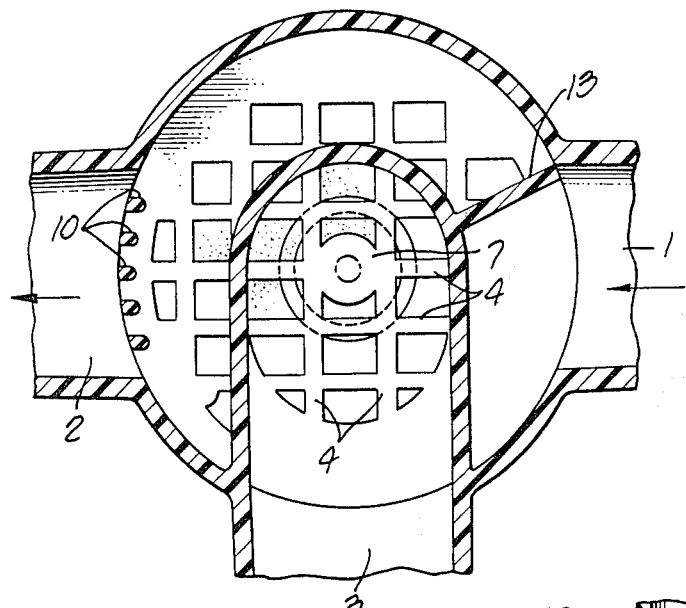
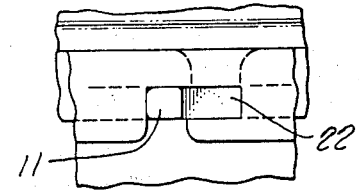
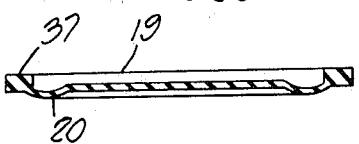
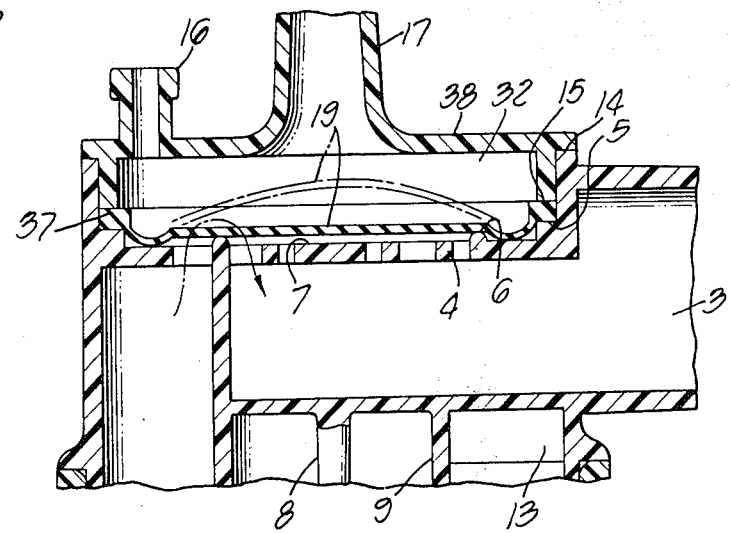
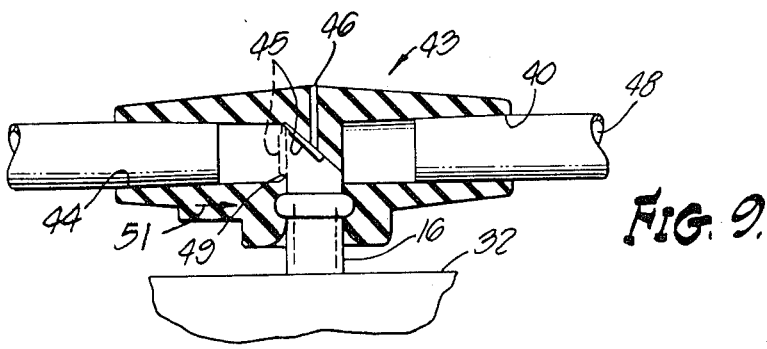

NEBULIZER-MANIFOLD

BACKGROUND OF THE INVENTION

This application is a continuation of my earlier filed U.S. application Ser. No. 750,510, filed Dec. 14, 1976 now abandoned, that was a continuation-in-part of my earlier filed U.S. application Ser. No. 635,902, filed Nov. 28, 1975 now abandoned, which was a continuation-in-part application of an earlier filed U.S. application Ser. No. 523,123, filed on Nov. 12, 1974 now abandoned.

This invention relates to a new and improved nebulizer-manifold device and more particularly relates to a disposable, preferably molded plastic, device having a minimum number of parts and improved performance.

Nebulizers are pneumatic devices for breaking up liquid medicament into small particles. Nebulizers entrain the small liquid particles in a stream of air or gas thereby providing an aerosol for inhalation therapy in the treatment of respiratory system disorders. It is important during such therapy that there be a sufficient quantity and proper formation of aerosol provided by the nebulizer. If the particles or droplets of the medicament are too fine, they are not likely to be retained in the respiratory tract, but will, to a great extent, be exhaled. If the particles are too large, they will likely be deposited on the upper reaches of the respiratory system, such as the trachea and the upper tracheal-bronchial tree, thereby leaving the rest of the system untreated. It is also important that the aerosol be delivered to the patient in a smooth, uniform manner.

Nebulizers are commonly employed by means of a manifold with an intermittant positive pressure breathing (I.P.P.B.) unit. Such an I.P.P.B. unit delivers a volume of gas at a controlled flow rate and pressure upon a detection in the I.P.P.B. unit outlet of a slight negative pressure, such as that caused by a patient's inhalation. Upon a predetermined pressure increase caused by the aeration of the lungs of the patient, the I.P.P.B. unit stops supplying gas and thereby allows the patient to completely exhale. I.P.P.B. units are normally constructed so that they can provide two gas streams, a high pressure nebulizing gas stream which is passed through the nozzle assembly of the nebulizer to form an aerosol and a low pressure main gas supply stream. The main gas supply stream carries the aerosol into the lungs of the patient.

Nebulizer-manifold devices typically employed a flexible membrane or diaphragm assembly to control the exhalation outlet. The diaphragm was generally positioned proximate to the exhalation outlet. During inhalation, the diaphragm was forced over the exhalation outlet by admitting pressurized gas from the I.P.P.B. machine into the exhalation chamber. Some prior devices used the high pressure nebulizing gas stream to force the diaphragm over the exhalation port. Unfortunately, in some cases, the high pressure of the nebulizing gas stream forced the diaphragm into the exhaust port of the nebulizer-manifold device thus causing a total failure of the device. One prior solution to this problem was to provide bleed orifices or openings from the exhalation chamber which vented to the atmosphere and functioned to reduce the pressure inside the chamber. Such bleed opening wasted the energy required to generate the initial higher pressure and the orifices in some cases became plugged thereby causing the nebulizer-manifold device to fail due to blockage of the supply of the gas or air stream. Moreover, such venting created objectionable operating noises caused by the escaping gas. The decrease in pressure by such venting resulted in decreased nebulizer efficiency.

The bleed openings also functioned to depressurize the exhalation chamber after inhalation. After inhalation, the flow of gas from the I.P.P.B. machine stops leaving residue pressure in the gas lines. The bleed openings depressurized the exhalation chamber. Upon depressurization, the diaphragm returns to its normal position thereby enabling the passage of the exhaled air through the exhalation outlet. Unfortunately the openings function to continuously depressurize the exhalation chamber rather than just during exhalation which resulted in excess noise and decreased efficiency.

Another solution to the problem of using the high pressure nebulizing gas stream to control the diaphragm was to utilize an I.P.P.B. machine which was equipped with a special low pressure line for controlling the diaphragm. Unfortunately, the use of the low pressure line required extra connections and tubing and it was still necessary to maintain the low pressure line at a higher pressure than the main gas supply stream to enable complete sealing of the exhalation outlet.

Another problem with disposable nebulizer-manifold devices previously used involves an inadequate mixing of the aerosol with the main gas supply stream from the I.P.P.B. unit. In prior devices the aerosol was merely added to the gas supply stream without any substantial diversion of the stream between the I.P.P.B. unit and the patient. Also during use and during exhalation, liquid medicament collects at the exhalation port in the nebulizer-manifold device and in those previous devices this collected liquid medicament discharges into the main gas supply stream and is thus wasted.

Still another problem associated with the disposable nebulizer-manifold devices used in the past was the cost of fabrication and assembly. Typically, such devices are comprised of several separately molded parts, all of which have to be assembled together. Moreover, in these devices the parts have not been sealed together and thus the devices are subject to disassembly by a patient or others with a resulting loss of parts or incorrect reassembly.

SUMMARY OF THE INVENTION

It is therefore a primary object of this invention to provide a low-cost disposable nebulizer-manifold device having improved operating characteristics.

Still another object of this invention is to provide a disposable nebulizer-manifold device which is simple and inexpensive to manufacture.

Other objects and advantages of this invention will be apparent from the following description and claims.

The disposable nebulizer-manifold device of the present invention produces aerosol and includes a manifold body positioned above a nebulizer unit having a nozzle assembly. The manifold body has a main supply inlet, and exhalation outlet and a patient connector port. A diaphragm assembly controls the opening and closing of the exhalation outlet. The diaphragm assembly is preferably operated by low pressure gas from the main gas supply line. The diaphragm assembly includes or cooperates with means which enable depressurization of the exhalation chamber upon completion of inhalation. The manifold body also includes main supply stream baffles, patient connector port grids, a nebulizer diffuser and a nebulizer containment baffle.

DESCRIPTION OF THE DRAWINGS AND PREFERRED EMBODIMENT

In the drawings:

FIG. 1 is a perspective view of the nebulizer-manifold device of the present invention;

FIG. 2 is a cross-sectional view of the nebulizer-manifold device taken along line 2—2 of FIG. 1;

FIG. 3 is a cross-sectional view of an alternate embodiment of a nebulizer-manifold device;

FIG. 6 is a perspective view of another alternate embodiment of the nebulizer-manifold device of the present invention;

FIG. 7 is a cross-sectional view of an exhalation outlet for the nebulizer-manifold device shown in FIG. 6;

FIG. 8 is a cross-sectional view taken along lines 8—8 of FIG. 6 and illustrates the diaphragm assembly;

FIG. 9 is a cross-sectional view of a valve assembly of the nebulizer-manifold device shown in FIG. 6;

FIG. 10 is a partial side view illustrating the locking of the nebulizer unit and manifold body of the device;

FIG. 11 is a cross-sectional view of a diaphragm for the nebulizer-manifold device;

Figure 4:
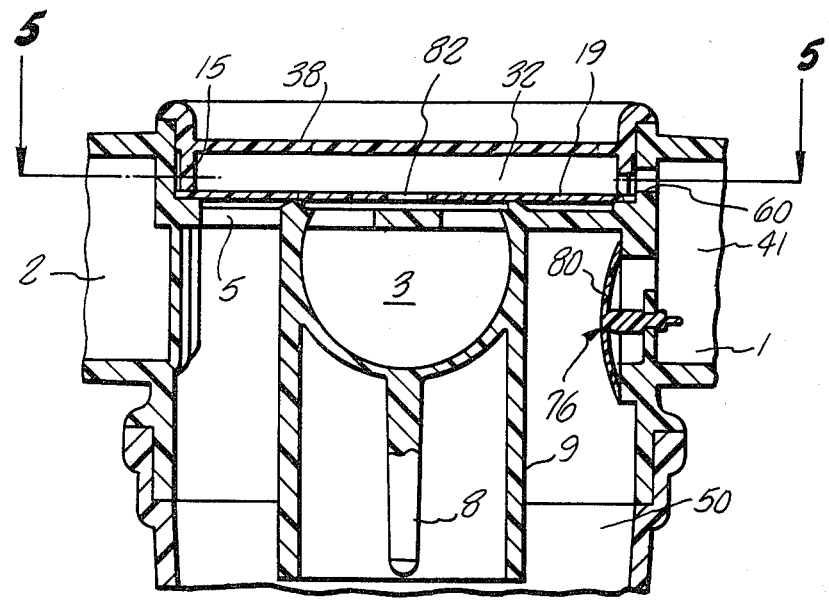
FIG. 4 is a cross-sectional view of another alternate embodiment of a nebulizer-manifold device.

Referring now to the drawings and more particularly to FIG. 1, a nebulizer-manifold device is shown connected to a main gas supply 1 of an intermittant positive pressure breathing (I.P.P.B.) machine (not shown). A patient connector port 2 of the device carries liquid medicament in a stream of gas to the user during inhalation and carries the exhaled gas from the user during exhalation. The patient connector port is normally adapted with a mouthpiece 52. Exhaled gases pass through the patient connector port, an exhalation chamber and finally exit the nebulizer-manifold device through an exhalation outlet 3. The exhalation outlet 3 is readily adaptable for connection to various pieces of apparatus capable of measuring and analyzing the exhalation stream.

Referring now to FIGS. 1 and 2, the nebulizer unit and its operation will be described in greater detail. Preferably, the nebulizer unit comprises a nozzle assembly of the type disclosed in my U.S. Pat. Nos. 3,097,645 and 3,762,409, the specifications of which are incorporated herein by reference. High pressure, air or gas from the nebulizing gas stream of the I.P.P.B. machine enters at nozzle assembly inlet 23. The nozzle assembly is provided with a collar 31 which is secured by hook members 30. Spray nozzle 27, in which a gas nozzle 24 is concentrically positioned, may be slightly tapered and tubular in shape. Medicament is allowed to enter from the liquid bowl reservoir 21 into the annular space between the spray nozzle 27 and the gas nozzle 24. The gas exits the gas nozzle 24 at gas orifice 25 and mixes with medicament in an opening between the spray nozzle 27 and gas nozzle 24. The mixture then passes through the spray orifice 28 and strikes a downwardly extending diffuser member 8. The space between the coaxial gas orifice 25 and the spray orifice 28 is properly determined and maintained by the seating pad 29. For a more detailed explanation of the nozzle assembly, including typical dimensional tolerances of the spray and gas nozzles, reference is made to my U.S. Pat. No. 3,762,409.

The nebulizer jet of medicament and gas passes into an open ended, cylindrically-shaped nebulizer jet containment baffle 9 wherein large liquid drops are collected on the chamber walls and returned to the nebulizer bowl 21. The mixture strikes diffuser member 8 which has a rounded base to facilitate dispersion of the drops of medicament. Preferably the diffuser member 8 and the open end of the nebulizer jet containment baffle 9 are spaced slightly below and coaxial with spray nozzle 27 and gas nozzle 24. The gas which is diverted into the bowl 21 and the medicament spray is allowed to intimately mix. Low pressure air or gas from the main gas stream of the I.P.P.B. machine enters the bowl 21 through main supply inlet 1. The incoming gas flows about the nebulizer jet containment baffle 9. This combined mixture of gas and medicament then passes through a slotted grid 10 which avoids the blow-through of large droplets of medicament and finally into the patient connector port 2.

Nebulization continues until the lungs of the user have been aerated to a predetermined pressure. Upon reaching this predetermined level, the I.P.P.B. machine senses this pressure level and the gas stream from the I.P.P.B. machine is automatically stopped and the user is allowed to exhale through the patient connector port 2 of the manifold body 41, through the exhalation chamber 32 and out the exhalation outlet 3.

The exhalation chamber 32 is divided into an upper portion and a lower portion by a diaphragm 19 which, in its normal position, preferably rests on diaphragm seal 6 overlying outlet 3 and is sealably secured by shoulder 5 of the manifold body 41 and a shoulder 15 of a cover member 38. The cover member 38 seats on the annular shoulder 14 of the manifold body. The cover member 38 preferably has an aperture 62 formed therein. The diaphragm is provided with a pop-up valve 64 which is disposed in aperture 62 of cover member 38. The pop-up valve 64 comprises stem 66 and cap 68.

Upon inhalation, gas from the main gas supply stream passes into inlet 1 and through passageway 60 into the upper portion of exhalation chamber 32 and forces diaphragm 19 downwardly sealing exhalation outlet 3 and pulling pop-up valve 64 downwardly, thereby closing aperture 62 with cap 68. In this closed position the diaphragm 19 seats against a diaphragm seal 6, thus preventing the nebulized stream entering patient connector port 2 from entering into exhalation outlet 3. The diaphragm 19 is retained in this position due to the surface differential area wherein the entire top of the diaphragm is subjected to a downward pressure and only a portion of the bottom of the diaphragm is subjected to an upward pressure. The gas from the main gas supply stream then flows into chamber 50 of bowl 21 around baffle 9 and exits the device through patient connector port 2. The nebulization continues until the lungs of the user have been aerated to a predetermined pressure. Upon reaching this predetermined level, the gas stream from the I.P.P.B. machine is automatically stopped and the user is allowed to exhale through the patient connector port 2. Upon the completion of inhalation, the pressure in the main chamber 50 of the nebulizer becomes equal to the pressure in the upper portion of chamber 32 and diaphragm 19 regains its original flat shape thereby opening aperture 62 of cover member 38. This enables venting of the upper portion of chamber 32 to the atmosphere through aperture 62. With the venting of the upper portion of chamber 32, the pressure in the main chamber forces diaphragm 19 slightly upward allowing the patient to exhale freely through the lower portion of chamber 32 and into exhalation outlet 3.

Referring to FIG. 3, there is shown a similarly formed nebulizer-manifold device. The device is comprised of a similarly shaped bowl containing a similarly formed nozzle assembly (not shown). The devices further comprising generally main gas supply inlet 1, manifold body 41, passageway 60, exhalation chamber 32 having diaphragm 19, overlying exhalation outlet 3 and cover member 38 having flanges 70 and aperture 62. The cover member is also provided with diaphragm 74 movably retained proximate to aperture 62 by flanges 70. Upon inhalation, gas from the main gas supply stream enters the upper portion of chamber 32 through passageway 60 and forces diaphragm 19 over outlet 3 and diaphragm 74 over aperture 62. Upon the completion of inhalation, the gas flow into chamber 32 ceases and diaphragm 74 drops down from aperture 62 onto flanges 70. The pressure in the upper portion of chamber 32 is then vented to the atmosphere through aperture 62. With the venting of chamber 32, the pressure in the main chamber of the nebulizer forces diaphragm 19 slightly upward allowing the patient to exhale through the lower portion of chamber 32 and into outlet 3.

Figure 5:
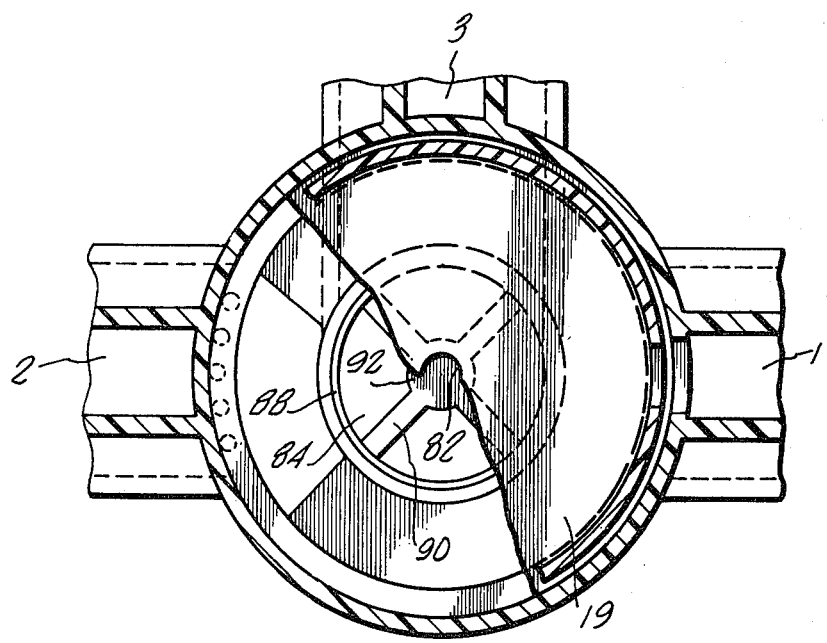
FIG. 5 is a cross-sectional view taking along lines 5—5 of FIG. 4.

Referring to FIGS. 4 and 5, there is shown another similarly formed nebulizer-manifold device. The device comprises generally main gas supply inlet 1, passageway 60, manifold body 41, containment baffle 9, diffuser member 8, patient connector port 2, exhalation chamber 32 having diaphragm 19 overlying exhalation outlet 3 and cover member 38. The main gas supply inlet 1 has a one way valve 76 disposed therein. The one way valve consists of a flexible material and comprises stem 78 which is attached to manifold body 41 and head 80. Diaphragm 19 is formed with a centrally located aperture 82. The diaphragm 19 is secured in chamber 32 between shoulder 15 of cover member 38 and shoulder 5 of the manifold body 41. When positioned in chamber 32, aperture 82 of the diaphragm 19 overlies passageway 84 connecting the chamber 32 to exhalation outlet 3. Passageway 84 is provided with valve seat 88 and with cross-hatching 90, and button 92 which functions to support the diaphragm during operation of the device. Aperture 82 of the diaphragm overlies button 92.

During inhalation gas from the main gas supply stream of the I.P.P.B. machine enters the device through main supply inlet 1 and forces one way valve 76 open. The gas also enters the upper portion of chamber 32 through passageway 60 and forces diaphragm 19 down to the bottom of the chamber onto valve seat 88, cross-hatching 90 and button 92 thereby preventing escape of the gas to the atmosphere through outlet 3. The diaphragm is retained in obstructing relation to passageway 84, because of the pressure in the upper portion of chamber 32 is slightly greater than the pressure in the main chamber 50 due to a slight pressure drop across one way valve 76. The diaphragm is also retained in this position due to the surface differential area. Upon the completion of inhalation, one way valve 76 closes. When the patient begins exhalation, the pressure in main chamber 50 becomes equal to the pressure in the upper portion of chamber 32 and diaphragm 19 regains its original flat shape. The pressure in the upper portion of chamber 32 is then vented to the atmosphere through aperture 82 in the diaphragm 19 and out through outlet 3. With the venting of the upper portion of chamber 32, the pressure in chamber 50 forces diaphragm 19 slightly upward allowing the patient to exhale freely through the lower portion of chamber 32 and passageway 84 and out through outlet 3.

Referring now to FIGS. 6–11, there is shown another alternate embodiment of a nebulizing device according to the present invention wherein the gas for controlling the exhalation chamber is obtained from the high pressure nebulizing gas stream rather than the low pressure main gas supply stream. The device similarly comprises main gas supply inlet 1, patient connector port 2, exhalation outlet 3, exhalation chamber 32 having disposed therein diaphragm 19, nebulizer bowl 21, manifold body 41 and cover member 38. The device is also provided with a control support post 17 and support ball 18 for holding or mounting the nebulizer-manifold device and the twist lock assembly, shown in more detail in FIG. 10, which comprises a bayonet lug type interlocking tongue 11 and groove 22. The twist lock assembly provides for the connection of the manifold body 41 and the nebulizer unit 21.

The venting and pressuring of the upper portion of chamber 32 is controlled by a valve member 43 shown in detail in FIG. 9. During inhalation, incoming pressurized air or gas from the nebulizing gas stream enters the valve 43 through a valve inlet 44. This forces a flapper check valve member 45 into its open position (shown solid in FIG. 9). A portion of the gas then passes into chamber 32 through inlet 16. The remaining gas is passed through valve 43 through tube 48 and passes to the nozzle assembly inlet 23. When the flapper 45 is in the open position, it seals off a vent 46 which is open to the atmosphere.

During exhalation the stream of air supplied to the valve inlet 44 is shut off and the flapper returns to its closed position 49 (shown dotted in FIG. 9). This change in the position of the flapper 45 allows the air or gas in the upper portion of the chamber 32 to vent to the atmosphere through vent 46 and thereby allowing the gases exhaled from the patient to lift the diaphragm 19 into its open position. In a preferred embodiment a restricted opening is provided between flapper 45 in its closed position and the body of valve 43, thus assuring adequate clearance for the flapper operation. Furthermore, the body of valve 43 is marked, as indicated by arrow 51, to show the direction of flow for proper operation of the valve.

Referring to FIGS. 7 and 8, when the gas stream from the I.P.P.B. is stopped upon reaching the predetermined level there is no longer any gas pressure sealing the diaphragm 19 over exhalation outlet 3 since the gas in the upper portion of chamber 32 is vented through vent 46. Exhaled gases thus pass through connector port 2, force the diaphragm 19 into its upper position as shown dotted in FIG. 8, and pass through the holes between grid member 4 and out through outlet 3.

Referring to FIG. 11, there is shown a diaphragm for use with a high pressure gas stream. The diaphragm 19 preferably has a thick outer rim 37 and a thin flexible area 20 radially surrounding a central area which seals all openings in the grid support made up of member 4.

This invention provides an inexpensive way to manufacture a durable nebulizer-manifold device which, because of its low cost of production, may be disposed of after use. Of particular significance is the fact that the entire device is comprised of separate molded parts and the diaphragm. During operation the gas from the I.P.P.B. machine is diverted into the bowl and thus there is no direct line of flow from the machine to the patient. Moreover, this diversion of the gas into the bowl promotes intimate mixing. The nozzle assembly of the nebulizer-manifold device operates at minimum noise levels, provides for proper control of the liquid medicament particles in the aerosol and promotes improved nebulization.

Having fully described my invention, it is to be understood that I do not wish to be limited to the details herein set forth, but my invention is of the full scope of the appended claims.

What is claimed is:

1. A device for controlling the flow of gas delivered to a patient with spray from a nebulizer component during inhalation and gas exhaled by the patient during exhalation, comprising:
   a body member having a gas inlet port, a patient connector port and an exhalation port with the gas delivered to the patient flowing from said gas inlet port to said patient connector port and the exhaled gas flowing from said patient connector port to said exhalation port;
   an exhalation control chamber defined by said body member and including a pressure sensitive member interposed between said exhalation port and said patient connector port during inhalation and thereby adapted to prevent the flow of gas into said exhalation port;
   means to cause said exhalation control chamber to be pressurized with gas having a pressure which is substantially equal to the gas pressure at the gas inlet port with the pressurization of said exhalation control chamber maintaining the interposition of said pressure sensitive member between said patient connector port and said exhalation port; and
   vent means in communication with said exhalation control chamber and operably connected with said pressure sensitive member to vent said exhalation control chamber during exhalation and cause said pressure sensitive member to move from between said patient connector port and said exhalation port thereby permitting flow of the exhaled gas therebetween.

2. A nebulizer-manifold device for introducing a spray into a low pressure main gas stream, comprising:
   a body member defining a nebulizer bowl and an exhalation control chamber including a cover member having an opening and a vent valve movably disposed in said opening, said body member including a main gas inlet, a patient connector port and an exhalation port;
   said main gas inlet and said patient connector port in open communication with said nebulizer bowl and through which gas from the low pressure main gas stream flows, said patient connector port adapted to be in communication with said exhalation port;
   a pressure sensitive member comprising a flexible diaphragm member separating said nebulizer bowl and said exhalation control chamber and extending across said exhalation port and adapted to close said exhalation port during an inhalation phase when the gas flows from said main gas inlet through said nebulizer bowl into said patient connector port; and
   a passageway communicating low pressure gas from said main gas inlet to said exhalation control chamber to close said exhalation port during the inhalation phase, said vent valve being connected to a flexing portion of said diaphragm member to thereby close said valve during an inhalation phase and to open said valve during an exhalation phase.

3. A nebulizer-manifold device for introducing a spray of medicament into a gas stream comprising:
   a manifold body including a nebulizer component which produces the spray and having a nebulizer bowl in communication with said nebulizer component and a cover member;
   a first main gas inlet and a patient connector port in open communication with said nebulizer bowl;
   an exhalation port in said manifold body and adapted to be in communication with said patient connector port;
   a flexible diaphragm extending across said exhalation port;
   an exhalation control chamber defined in part by said cover member and said flexible diaphragm and during inhalation interposed between said exhalation port and said patient connector port;
   a second gas inlet in communication with said first main gas inlet and said exhalation control chamber with said flexible diaphragm closing said exhalation port during inhalation when gas is supplied to said exhalation chamber from the main gas supply stream through said second gas inlet; and
   means in said exhalation chamber capable of venting pressure in said exhalation chamber only during exhalation comprising a pop-up valve movably disposed in an opening formed in said cover member and connected to a flexing portion of said diaphragm.

4. The device of claim 3 wherein the pressure of the gas supplied to said exhalation control chamber through said second gas inlet is substantially equal to the pressure of the gas supplied to said nebulizer bowl through said first main gas inlet.

5. A nebulizer-manifold device for introducing a spray of medicament into a gas stream comprising:
   a manifold body including a nebulizer component which produces the spray and having a nebulizer bowl in communication with said nebulizer component and a cover member;
   a first main gas inlet and a patient connector port in open communication with said nebulizer bowl;
   an exhalation port in said manifold body and adapted to be in communication with said patient connector port;
   a flexible diaphragm extending across said exhalation port;
   an exhalation control chamber defined in part by said cover member and said flexible diaphragm and during inhalation interposed between said exhalation port and said patient connector port;
   a second gas inlet in communication with said first main gas inlet and said exhalation control chamber with said flexible diaphragm closing said exhalation port during inhalation when gas is supplied to said exhalation chamber from the main gas supply stream through said second gas inlet wherein the pressure of said gas supplied to said exhalation control chamber is substantially equal to the pressure of the gas supplied to said nebulizer bowl through the said first main gas inlet; and
   means in said exhalation chamber capable of venting pressure in said exhalation chamber only during exhalation comprising a pop-up valve movably disposed in an opening formed in said cover member and connected to a flexing portion of said diaphragm.

6. A nebulizer-manifold for introducing a spray into a low pressure main gas stream, comprising:
- a body member defining a nebulizer bowl and an exhalation control chamber and including a main gas inlet, a patient connector port and an exhalation port, said main gas inlet and said patient connector port in open communication with said nebulizer bowl and through which gas from the low pressure main gas stream flows, said exhalation port adapted to be in communication with said patient connector port, said exhalation control chamber including a cover member having an opening and a vent valve including a pop-up valve movably disposed in said opening;
- a pressure sensitive member comprising a flexible diaphragm member separating said nebulizer bowl and said exhalation control chamber and extending across said exhalation port and adapted to close said exhalation port during an inhalation phase when the gas flows from said main gas inlet through said nebulizer bowl and into said patient connector port; and
- means for connecting low pressure gas from said main gas inlet to said exhalation control chamber to close said exhalation port during the inhalation phase, the pop-up valve being connected to a flexing portion of said flexible diaphragm member, said vent valve being adapted to close during the inhalation phase and to open during an exhalation phase.

7. A nebulizer-manifold device for introducing a spray into a main gas stream having a first pressure, the nebulizer-manifold connected to a second gas stream having a second pressure for the generation of said spray, the nebulizer-manifold device comprising:
- a body member defining a nebulizer bowl and an exhalation control chamber and having nebulizer means within the nebulizer bowl in communication with the second gas stream having the second pressure;
- a main gas inlet and a patient connector port through which the main gas stream flows and in open communication with said nebulizer bowl and a sinuous passageway extending therebetween;
- an exhalation port adapted to be in communication with said patient connector port;
- a diaphragm member separating said exhalation control chamber and said nebulizer bowl and extending across said exhalation port and adapted to close said exhalation port during the inhalation phase;
- means to pressurize said exhalation control chamber with the first pressure of the main gas stream from said main gas port to cause said diaphragm to close said exhalation inlet; and
- a vent valve in communication with said exhalation control chamber, said vent valve including a valve member operably connected to a flexing portion of said diaphragm member and a venting aperture in the exhalation control chamber, the vent valve adapted to close the venting aperture during the inhalation phase and to open the venting aperture during the exhalation phase.

* * * * *